(12) United States Patent
Weber (10) Patent No.: US 9,440,003 B2
(45) Date of Patent: Sep. 13, 2016

(54) MEDICAL DEVICES HAVING PARTICLE-CONTAINING REGIONS WITH DIAMOND-LIKE COATINGS

(75) Inventor: Jan Weber, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 3077 days.

(21) Appl. No.: 11/266,862

(22) Filed: Nov. 4, 2005

(65) Prior Publication Data

US 2007/0106363 A1    May 10, 2007

(51) Int. Cl.
  A61L 27/30   (2006.01)
  A61L 29/10   (2006.01)
  A61L 31/08   (2006.01)
  B82Y 30/00   (2011.01)

(52) U.S. Cl.
  CPC ............ *A61L 27/303* (2013.01); *A61L 29/103* (2013.01); *A61L 31/084* (2013.01); *B82Y 30/00* (2013.01); *A61L 2400/12* (2013.01)

(58) Field of Classification Search
  None
  See application file for complete search history.

(56) References Cited

U.S. PATENT DOCUMENTS

| | | | |
|---|---|---|---|
| 4,842,598 A * | 6/1989 | Tran | 604/891.1 |
| 5,112,900 A | 5/1992 | Buddenhagen et al. | |
| 5,123,924 A * | 6/1992 | Sioshansi et al. | 424/423 |
| 5,203,804 A * | 4/1993 | Nikutowski et al. | 433/8 |
| 5,348,538 A | 9/1994 | Wang et al. | |
| 5,403,340 A | 4/1995 | Wang et al. | |
| 5,447,497 A | 9/1995 | Sogard et al. | |
| 5,482,601 A | 1/1996 | Ohshima et al. | 204/173 |
| 5,490,962 A * | 2/1996 | Cima et al. | 264/401 |
| 5,549,552 A | 8/1996 | Peters et al. | |
| 5,550,180 A | 8/1996 | Elsik et al. | |
| 5,556,383 A | 9/1996 | Wang et al. | |
| 5,593,719 A | 1/1997 | Dearnaley et al. | |
| 5,604,038 A | 2/1997 | Denes et al. | |
| 5,705,233 A | 1/1998 | Denes et al. | |
| 5,725,573 A | 3/1998 | Dearnaley et al. | 623/2 |
| 5,830,182 A | 11/1998 | Wang et al. | |
| 5,858,477 A | 1/1999 | Veerasamy et al. | |
| 5,908,539 A | 6/1999 | Young et al. | |
| 5,945,153 A | 8/1999 | Dearnaley | |
| 5,951,941 A | 9/1999 | Wang et al. | |
| 6,054,018 A | 4/2000 | Denes et al. | |
| 6,082,292 A | 7/2000 | Denes et al. | |
| 6,096,564 A | 8/2000 | Denes et al. | |
| 6,146,356 A | 11/2000 | Wang et al. | |
| 6,171,278 B1 | 1/2001 | Wang et al. | |
| 6,277,480 B1 * | 8/2001 | Veerasamy et al. | 428/217 |
| 6,328,925 B1 | 12/2001 | Wang et al. | |
| 6,406,457 B1 | 6/2002 | Wang et al. | |
| 6,531,182 B2 | 3/2003 | Veerasamy et al. | |
| 6,562,445 B2 | 5/2003 | Iwamura | |
| 6,572,651 B1 | 6/2003 | De Scheerder et al. | |
| 6,592,519 B1 | 7/2003 | Martinez | |
| 6,607,598 B2 | 8/2003 | Schwarz et al. | |
| 6,660,340 B1 | 12/2003 | Kirkpatrick | |
| 6,696,157 B1 | 2/2004 | David et al. | |
| 6,709,463 B1 | 3/2004 | Pope et al. | |
| 6,761,736 B1 | 7/2004 | Woo et al. | |
| 6,994,907 B2 | 2/2006 | Resasco et al. | 428/367 |
| 7,498,365 B2 * | 3/2009 | Muratoglu et al. | 524/81 |
| 7,498,924 B2 * | 3/2009 | Scherabon | 340/10.2 |
| 2001/0001128 A1 | 5/2001 | Holman et al. | |
| 2002/0026899 A1 | 3/2002 | McLaughlin et al. | 118/723 |
| 2002/0062133 A1 | 5/2002 | Gilson et al. | |
| 2002/0068170 A1 | 6/2002 | Smalley et al. | 428/403 |
| 2002/0082674 A1 | 6/2002 | Anson et al. | |
| 2002/0165405 A1 | 11/2002 | Peng et al. | 556/57 |
| 2003/0065355 A1 | 4/2003 | Weber | |
| 2003/0069632 A1 | 4/2003 | De Scheerder et al. | 623/1.15 |
| 2003/0159920 A1 * | 8/2003 | Roth | 204/192.12 |
| 2003/0236514 A1 | 12/2003 | Schwarz | 604/890.01 |
| 2004/0073251 A1 | 4/2004 | Weber | 606/194 |
| 2004/0138733 A1 * | 7/2004 | Weber et al. | 623/1.11 |
| 2004/0148007 A1 | 7/2004 | Jackson et al. | |
| 2004/0185116 A1 | 9/2004 | Hill et al. | 424/617 |
| 2005/0033418 A1 | 2/2005 | Banas et al. | 623/1.49 |
| 2005/0089706 A1 * | 4/2005 | Urata et al. | 428/546 |
| 2005/0096509 A1 * | 5/2005 | Olson | 600/300 |
| 2005/0240254 A1 | 10/2005 | Austin | |
| 2005/0260355 A1 | 11/2005 | Weber et al. | 427/566 |
| 2006/0079863 A1 | 4/2006 | Burgmeier et al. | |

FOREIGN PATENT DOCUMENTS

| | | |
|---|---|---|
| EP | 0876821 | 11/1998 |
| GB | 2287473 A | 9/1995 |
| JP | 11106920 | 4/1999 |
| JP | 2003310744 | 5/2003 |
| JP | 2003000527 | 7/2003 |
| WO | 0143790 A2 | 6/2001 |
| WO | WO 01/43790 * | 6/2001 |
| WO | WO 0143790 A2 * | 6/2001 |
| WO | 2004096085 A2 | 11/2004 |

(Continued)

OTHER PUBLICATIONS

Definitions for: particle, region and layer; Merriam Webster's Online Dictionary downloaded from <www.merriam-websters.com> on Jul. 12, 2009, pp. 1-3.*

(Continued)

*Primary Examiner* — David J Blanchard
*Assistant Examiner* — Ivan Greene
(74) *Attorney, Agent, or Firm* — Seager, Tufte & Wickhem, LLP (57) ABSTRACT

According to an aspect of the present invention, various medical devices, including implantable or insertable medical devices, are provided, which comprise at least one particle-containing region whose surface is at least partially coated with a diamond-like coating.

25 Claims, 7 Drawing Sheets

(56) References Cited

FOREIGN PATENT DOCUMENTS

| WO | 2005037985 A2 | 4/2005 | |
|---|---|---|---|
| WO | WO 2005/046749 A1 | 5/2005 | A61L 29/10 |
| WO | WO 2005/112845 A1 | 12/2005 | A61F 7/12 |

OTHER PUBLICATIONS

Definitions for: particle, fundamental particle, interface, surface, surface chemistry, stainless steel and chromium; Hawley's Condensed Chemical Dictionary (14th edition); Lewis, Richard J., Sr.; John Wiley & Sons, 2002; pp. 1-8.*
Kaner, Richard B.; Gilman, John J.; Tolbert, Sarah H.; Designing Superhard Materials; 2005; AAAS; Science, vol. 308, pp. 1268-1269.*
Sreekumar, T.V.; Liu, Tao; Kumar, Satish; Single-Wall Carbon Nanotube Films; 2003; ACS; Chemistry of Materials, vol. 15, pp. 175-178.*
Robertson, J.; Diamond-like carbon; 1994; IUPAC; Pure and Applied Chemistry, vol. 66, No. 9, pp. 1789-1798.*
Schittenhelm, H.; Geohegan, D. B.; Jellison, G. E.; Puretzky, A. A.; Lance, M. J.; Britt, P. F.; Synthesis and characterization of single-wall carbon nantube-amorphous diamond thin-film composites; 2002; American Institute of Physics; Applied Physics Letters, vol. 81, No. 11, pp. 2097-2099.*
Merriam-Websters Collegiate Dictionary, $11^{th}$ ed. (2004) entries for "derivative", "energize" and "particulate", pp. 336, 413 and 904.*
Wikipedia The Free Encyclopedia, entry for information "About" Wikipedia, retrieved from <en.wikipedia.org> on Mar. 19, 2013; pp. 1-18.*
Schittenhelm, H.; Geohegan, D. B.; Jellison, G. E.; Puretzky, A. A.; Lance, M. J.; Britt, P. F. Synthesis and characterization of single-wall carbon nantube-amorphous diamond thin-film composites; 2002; American Institute of Physics; Applied Physics Letters, vol. 81, No. 11, pp. 2097-2099.*
Jennifer A. Lewis, "Direct-Write Assembly of Ceramics from Colloidal Inks," *Current Opinion in Solid State and Materials Science*, 6 (2002) pp. 245-250.
Jennifer A. Lewis, et al., "Direct Writing in Three Dimensions," *Materials Today*, Jul./Aug. 2004, pp. 32-39.
V.A. Izumrudov, et al., The Formation Reactions of Non-Stoichiometric Polyelectrolyte Complexes, *Polymer Science U.S.S.R.*, vol. 25, No. 9, 1983, pp. 2296-2304.
A History of Body Armore-Bullet Proof Vests, downloaded from on Feb. 28, 2005. http://inventors.about.com/library/inventors/blforensic3.htm.
X. L. Fennandez, "Theoretical Study of the Bascity and the Redox Properties of Heteropolyanions," downloaded on Mar. 1, 2005, 74 pages.
Ivan Kozhevnikov, "Catalysts for Fine Chemical Synthesis, vol. 2, Catalysis by Polyoxometalates", Hardcover, Oct. 2002, 8 pages.
V.A. Izumrudov, et al., "Specific Features of Complex Interchange Reactions Between Polyelectrolytes", *Visokomol. Soyed*, A29 (6), 1987, pp. 1224-1230, 2 pages.
N. K. Nefedov, et al., *Visokomol. Soyed*, A27 (7), 1985, p. 1677.
H. Schittenhelm, et al., "Synthesis and Characterization of Single-Wall Carbon Nanotube—Amorphous Diamond Thin-Film Composites,"*Applied Physics Letters*, vol. 81, No. 11, Sep. 9, 2002, pp. 2097-2099.
"Carbon Nanotube Bucky Paper Scaffold for Retinal Cell Transplantation," NASA Ames Research Center, 2 pages, Jan. 6, 2003.
D.B. Geohegan, et al., "Multifunctional Nanotube Composites," Oak Ridge National Laboratory, Laboratory Directed Research and Development Program, Fy 2003, Annual Report, pp. 26-30.
G. M. Spinks, et al., "Pneumatic Actuator Response from Carbon Nanotube Sheets," *Materials Research Society Symposium Proceedings*, 2002, vol. 706, pp. Z9.22.1-6.
A. G. Rinzler, et al., "Large Scale Purification of Single-Wall Carbon Nanotubes: Process, Product, and Characterization," *Applied Physics A*, A67, pp. 29-37 (1998).
K. D. Ausman, et al., "Organic Solvent Dispersions of Single-Walled Carbon Nanotubes: Towards Solutions of Pristine Nanotubes," *J. Physical Chem.*, vol. 104, No. 38, pp. 8911-8915 (2000).
T. V. Sreekumar, et al., "Single-Wall Carbon Nanotube Films," *Chem. Mater.*, 15:175-178 (2003).
V. Skakalova, et al. "Gamma-Irradiated and Functionalized Single Wall Nanotubes," *Diamond and Related Materials*, 13, pp. 296-298 (2004).
Urszula Dettlaff-Weglikowska, et al., "Enhancement of Conductivity of Bucky Paper by Chemical Modification" Symposium HH, Functional Carbon Nanotubes, 2004 MRS Fall Meeting, Boston Massachusetts, USA. Abstract HH13.36.
P. B. Mirkarimi, et al., "Review of Advances in Cubic Boron Nitride Film Synthesis," *Materials Science and Engineering*, R21 (1997), pp. 47-100.
S. Aoqui, et al., "Preparation of Boron Carbide Thin Film by Pulsed KrF Excimer Laser Deposition Process," *Thin Solid Films* 407 (2002), pp. 126-131.
Y.A. Elabd, et al., "Transport Properties of Triblock Copolymer Ionomer Membranes for Fuels Cells," *J. Membrane Sci.*, 23rd Annual Army Science Conference Oral Paper AO-02 (2002), 8 pages.
Nasa Tech Briefs: "Fluorinated Diamondlike Carbon Coatings", Copyright Oct. 2001, 1 page. http://www.findarticles.com/p/articles/mi_qa3957/is_200110/ai_n8967401/print.
J. Robertson, "Diamond-Like Carbon," *Pure & Appl. Chem.*, 1994, vol. 66, No. 9, pp. 1789-1796.

* cited by examiner

MEDICAL DEVICES HAVING PARTICLE-CONTAINING REGIONS WITH DIAMOND-LIKE COATINGS

FIELD OF THE INVENTION

This patent application relates to medical devices, including implantable or insertable medical devices, having particle-containing regions with diamond-like coatings.

BACKGROUND OF THE INVENTION

Implantable and insertable medical devices are well known in the medical community. Many of these devices are configured to expand upon implantation or insertion into the body. For instance, angioplasty procedures are well known, in which a catheter is navigated through a lumen of a vertebrate subject to a site needing expansion. For example, a distal portion of a catheter containing a deflated balloon may be directed to an area of an artery that is substantially blocked, and that may be enlarged upon expansion of the balloon, typically by a hydraulic or pneumatic mechanism.

U.S. Patent Appln. Pub. No. 2004/0138733, the entire disclosure of which is hereby incorporated by reference, describes medical devices, which include the use of nanopaper for mechanical actuation. The medical devices may be provided, for example, in the form of a balloon catheter, in which the nanopaper is mounted about an electrode and into which an electrically conductive solution is dispersed. Actuation of the electrode causes generation of bubbles, which in turn causes the nanopaper, and thus the medical device to which it is applied, to expand. Whereas inner bubbles are generally trapped and act to expand the nanopaper, an issue encountered with devices of this type is that bubbles created at the outer surfaces may escape into the surrounding media. Without wishing to be bound by theory, it is believed that, due to the very high surface area of the carbon nanotubes, bubbles can arise at many locations throughout the nanopaper. Small bubbles have tremendous inner pressure. Normally when they contact one another, smaller bubbles merge to form larger ones as the pressure is decreased inside the larger bubbles. However in the case of nanopaper, bubbles cannot merge together due to the network of carbon nanotubes. They can only merge if they crack open the carbon nantube paper. The bubbles on the surface of the paper, however, don't have the restriction of being surrounded by carbon nanotubes and can readily merge together to become larger. If they get large enough, their upward force (due to gravity) eventually becomes larger then the adhesion force which keeps them sticking to the paper surface, and the bubbles depart from the surface.

Even if the actuator is sheathed, it is desirable to prevent bubbles from escaping from the surface as they and expand the sheath. For example, if the sheath happened to burst, this would allow the gas between the sheath and the nanopaper to escape into the body. If this occurs at high pressure, the gas bubbles will expand due to a drop in pressure and may cause a blockage in the arteries.

Other implantable and insertable medical devices are adapted to achieve enhanced or suppressed interactions with surrounding cells and tissue. For example, carbon nanotube materials have been shown to be an ideal matrix for endothelial cell growth. See, e.g., "Carbon Nanotube Bucky Paper Scaffold for Retinal Cell Transplantation," NASA Ames Research Center, including spatial organization. This is likely due, at least in part, to the nanostructure and porosity of such materials. For example, it is known that nanostructured surfaces may directly interact with cell receptors, thereby controlling the adhesion or non-adhesion of cells to the surface. It is also noted that carbon nanotube materials are porous and therefore may allow for the flow of therapeutic agents, including growth factors and nutrients.

However, the mechanical robustness of many particle-based materials, including paper formed from carbon nanotubes, is in need of enhancement.

SUMMARY OF THE INVENTION

The invention is directed to medical devices which include a diamond-like coating over at least a portion of their surfaces. According to an aspect of the present invention, various medical devices, including various implantable or insertable medical devices, are provided, which comprise at least one particle-containing region whose surface is at least partially coated with a diamond-like coating. In some embodiments, the particle-containing region is conductive. In some embodiments, the particle-containing region contains a therapeutic agent.

An advantage of this invention is that medical devices having particle-containing regions may be provided, in which the robustness of the particle-containing region is improved.

Another advantage of this invention is that medical devices having expandable particle-containing regions, for example, carbon-particle-containing regions, may be provided in which bubble formation at (and hence bubble loss from) the outer surfaces of the particle-containing regions is reduced or prevented.

These and other embodiments and advantages of the present invention will become readily apparent to those of ordinary skill in the art upon review of the Detailed Description and Claims to follow.

DETAILED DESCRIPTION

A more complete understanding of the present invention is available by reference to the following detailed description of various aspects and embodiments of the invention. The detailed description of the invention which follows is intended to illustrate but not limit the invention.

According to an aspect of the present invention, medical devices, including various implantable or insertable medical devices, are provided, which comprise at least one particle-containing region whose surface is at least partially coated with a diamond-like coating.

Medical devices which may be provided with such diamond-coated particle-containing regions include implantable or insertable medical devices, which can be selected, for example, from the following: catheters (e.g., renal or vascular catheters such as balloon catheters), guide wires, balloons, filters (e.g., vena cava filters), filter wires, stents (e.g., coronary vascular stents, peripheral vascular stents, cerebral, urethral, urethral, biliary, tracheal, gastrointestinal and esophageal stents), bifurcation stents, stent grafts, stent delivery catheters, vascular grafts, vascular access ports, embolization devices including cerebral aneurysm filler coils (including Guglilmi detachable coils and metal coils), intravascular occlusion devices, septal defect devices, myocardial plugs, Y-adapters, patches, pacemakers and pacemaker leads, left ventricular assist hearts and pumps, total artificial hearts, heart valves, vascular valves, shunts, drain tubes, urinary sphincters, urinary dilators, penile prosthesis, distal protection devices, biopsy devices, and any coated substrate (which may comprise, for example, glass, metal, polymer, ceramic and combinations thereof) that is implanted or inserted into the body. Further examples of medical devices include sutures, suture anchors, anastomosis clips and rings, tissue staples and ligating clips at surgical sites; cannulae, metal wire ligatures, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery, tissue bulking devices, and tissue engineering scaffolds for cartilage, bone, skin and other in vivo tissue regeneration.

The diamond-coated particle-containing regions may, for example, be disposed over all or a portion of a substrate (e.g., a metallic substrate or a non-metallic substrate, such as a polymeric or ceramic substrate) that corresponds to a medical device or a portion of a medical device, or they may constitute the bulk of the medical device (e.g., in the case of a tissue engineering scaffold).

The diamond-coated particle-containing regions may be provided, for example, within the medical device (e.g., beneath a hydrogel coating, a balloon, a polymeric sheath, etc.) or at the medical device surface (e.g., on a balloon surface, a stent surface, a sheath surface, etc.).

Particle-containing regions may be employed in medical devices for a variety of reasons. One specific example of a particle-containing region is a conductive nanopaper region, which, as noted above, may be used for mechanical actuation. One specific example of a medical device that employs such an actuator is shown in longitudinal and lateral cross-sections, respectively, in FIGS. 1A and 1B. The medical device may comprise an axis 111 and proximal 115 and distal 117 regions. The distal end is the end navigated through a lumen or other passageway of the body of a human or other vertebrate subject for the performance of various medical procedures. Near the distal end 117, a housing 112 (e.g., comprising a balloon 120, in the present embodiment) may be provided, having a proximal end 114 and a distal end 116, which comprises one or more actuators 130, 150, forming an expandable assembly 118.

Although the actuators 130, 150 may appear superfluous in light of the balloon 120, this is not the case. In particular, balloon catheters can be described as having a hydraulic actuating mechanism. Because hydraulic systems are more efficient at larger dimensions, the present trend to downscale device sizes has created the need for actuators that efficiently function at very small diameters. Conductive nanopaper actuators meet this criterion.

Figure 1A:
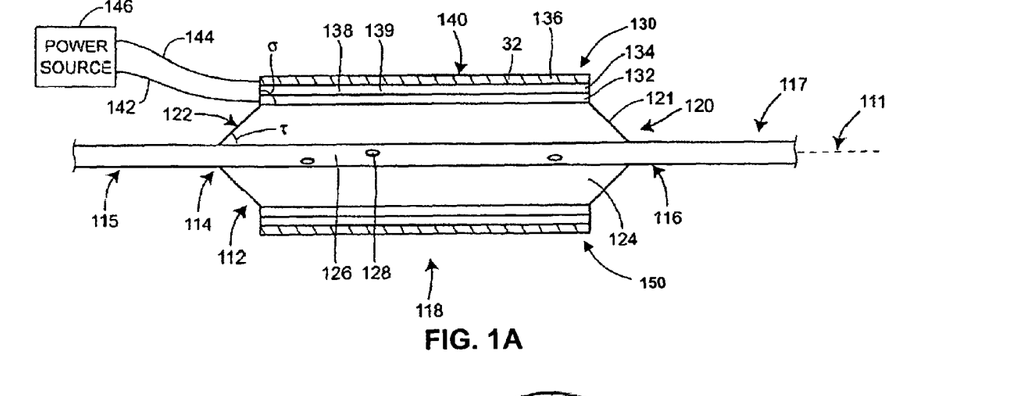
FIGS. 1A and 1B are schematic cross-sectional longitudinal and lateral views, respectively, of a balloon assembly having actuators on its outer surface, which are depicted in a contracted or non-actuated state, in accordance with an embodiment of the present invention.
Figure 1B:
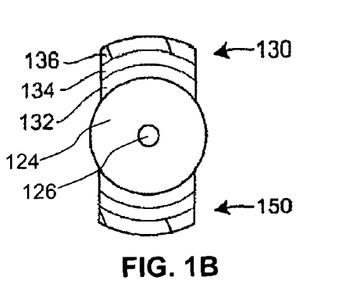

Although FIG. 1B illustrates a first and second actuator 130, 150 diametrically opposed to one another this number and arrangement is for illustrative purposes only, as particular embodiments may have any number of actuators in any number of different arrangements and orientations.

Embodiments comprising more than one actuator may be configured so that the individual actuators may be activated collectively or independently. In some embodiments, multiple groups of actuators may each be activated collectively, with each group being capable of being activated independently of the other groups.

While an electrically actuated medical device for use in enlarging lumens is shown (e.g., an angioplasty balloon catheter system), it is to be understood that electromechanical actuation may be used in conjunction with essentially any type of medical device, including those described herein, for which expansion is useful, such as, for example, expandable stents, aneurysm filler coils, guidewires, and septal closure devices, expandable devices for deploying other medical devices, devices for taking biopsy samples, among many others.

The particular device illustrated comprises a balloon 120 having an outer perimeter 113. Either pneumatic or hydraulic balloons may be used, or both. The balloon 120 may comprise an exterior surface 122 and an interior 124. The device may comprise an interior tube 126 in the interior 124. The interior tube 126 may provide one or more apertures 128 that allow inflation media to enter the balloon 120 from the interior tube 126, i.e., in its role as an inflation lumen. (Note that, unlike the remainder of the figure, the interior tube 126 of FIG. 1A is not shown in cross-section so as to allow the illustration of the apertures 128. The same applies to FIGS. 1C, 2A, 2C, and 8A below.) The interior tube 126 may also provide a lumen for a guidewire or other components including, for example, conductors 142, 144 for operating the actuators 130, 150. While the balloon 120 is shown inflated, this is for illustrative purposes only, and in some embodiments the balloon 120 may be inflated after the actuator 130, 150 is activated or balloon 120 inflation may occur simultaneously with actuator 130, 150 activation.

The actuator 130 may comprise a first electrode 132 and a second electrode 136. Suitable conductive materials for the first electrode 132 are described below. In some embodiments, the function of the first electrode 132 may by be performed by a conductive balloon wall 121. The second electrode 136 may comprise, for example, a particle-containing conductive region with a diamond-like coating provided at its outer surface 140, as described in more detail below. A separator 134, such as one of those described in more detail below, is provided between the first 132 and second 136 electrodes.

An electrolyte 138 is provided in the actuator 130 so as to allow for a completed electrical circuit between the first and second electrodes 132, 136. The electrolyte 138 may be supported by a suitable fluid 139 as described below. The electrolyte 138 and fluid 139 are operatively associated with the separator 134 and first and second electrodes 132, 136. In the embodiment shown, the electrolyte 138 provides an ion that allows for formation of a gas upon activation of the actuator 130, e.g., formation of oxygen, chlorine, or other gas, causing expansion of the second electrode 136. Being an electrochemical process, gas bubble formation does not occur at non-conductive surfaces. Consequently, gas bubble formation is impeded or eliminated at the outer surface, where the particle-containing conductive region is provided with the diamond-like coating, which is non-conductive. As noted above, bubbles created at the outer surfaces are likely to escape into the surrounding media.

The first and second electrodes 132, 136 may be operatively associated with a power source 146 by means of the first and second electrical conductors 142, 144, respectively. The power source 146 may be immediately adjacent to the actuator 130 or may be present in a proximal region 115 or distal region 117 of the medical device. The power source 146 may also be external to the subject during the medical procedure. The conductors 142, 144 may be formed of any suitable conductive material, such as those as described below.

Figure 1C:
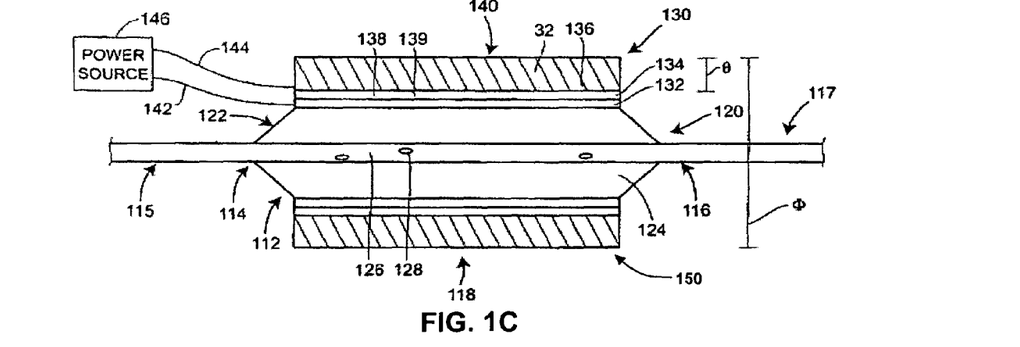
FIGS. 1C and 1D are the views of FIGS. 1A and 1C, respectively, in which the actuators are depicted in an expanded or actuated state.
Figure 1D:
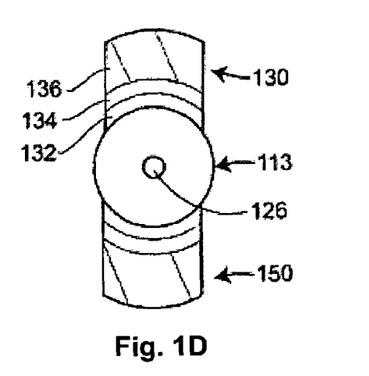

During operation, the power source 146 may be actuated so as to apply, via conductors 142 and 144, a voltage that is sufficient to form bubbles at the second electrode 136, for example, a voltage on the order of about 1.0 to 1.2 Volts. FIGS. 1A and 1B, are schematic partial longitudinal and lateral sectional views of the medical device with the actuators 130, 150 in a non-activated state. FIGS. 1C and 1D, on the other hand, show the same views with the actuators 130, 150 in an activated state. As depicted in FIGS. 1C and 1D, activation of the actuator expands the thickness θ of the second electrode 136, which consequently increases the overall width φ of the expandable assembly 118.

In operation, the medical device of FIGS. 1A-D may be employed for medical procedures such as, for example, an angioplasty procedure wherein the assembly 118 is navigated through a body lumen (not shown) of a vertebrate subject until it is appropriately positioned, such as within a blocked area of an artery. Once positioned, the power source 146 directs a voltage (and passes a current), via conductors 142 and 144, that is sufficient to form bubbles within the second electrode 136, causing it to expand. The procedure may also comprise the step of deactivating the actuators 130, 150 by reversing the voltage sufficiently such that the electrochemical reactions are reversed and the bubbles are removed, thereby reversing the expansion of the actuators 130, 150. On the other hand, actuator may be left in an activated state indefinitely, although over time the actuator may return to a deactivated state without reversing potential.

Figure 8A:
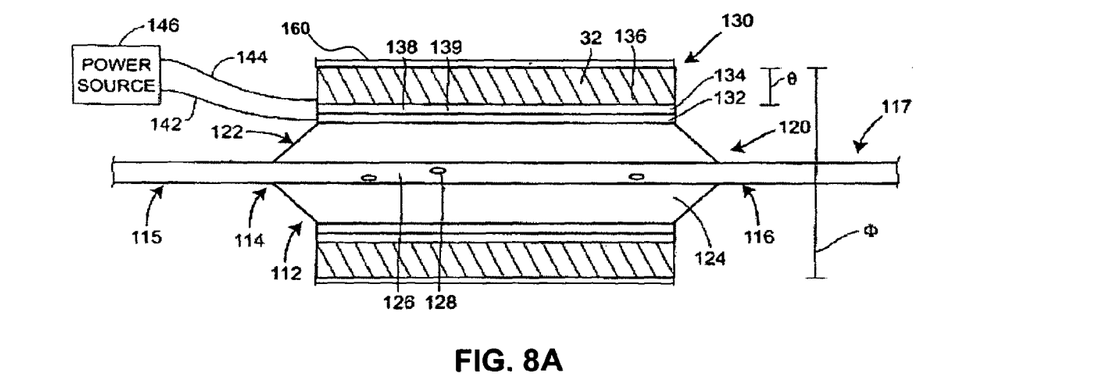
FIGS. 8A and 8B are schematic cross-sectional longitudinal and lateral views, respectively, of a balloon assembly having actuators on its outer surface, which are depicted in a in an expanded or actuated state. These drawings are analogous to those of FIGS. 1C and 1D, except that the assembly is further provided with an elastic sheath.
Figure 8B:
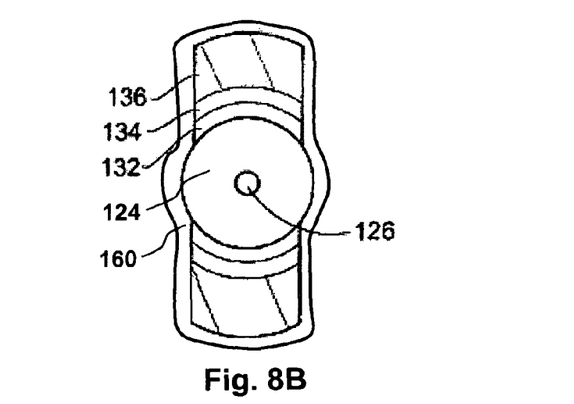

In some embodiments, the device may be provided with an elastic sheath 160, as illustrated in FIGS. 8A and 8B. An advantage of an outer elastic sheath is that it may expand as the second electrode 136 expands, yet it may also act to recompress the second electrode 136 to a reduced diameter, which may be approximately its original diameter before activation. Once back to a reduced diameter, the assembly 118 may be withdrawn from the lumen, or reactivated. A sheath is not necessary for reduction of diameter, but may be used to accelerate collapse.

In some embodiments, the expansion of the balloon may be made permanent by means including settable gels and mechanical mechanisms, such as those described, for example, in U.S. Patent Appln. Pub. No. 2004/0138733. For example, the balloon may be a detachable balloon that is used to plug various body lumens, for example, blood vessels.

In some embodiments, one or more actuators are disposed not around an outer perimeter of the balloon 120, but rather within the interior 124 of the balloon 120, for example, either being disposed on an inner surface of the balloon wall 121 or disposed around the interior tube 126 in the interior 124. In either latter case, the actuator 130 may be deployed when the balloon 120 is in a collapsed state, in which case the actuator 130 will expand the balloon 120 outward from a fully crimped state to a second partially expanded state. As its diameter is increased, the balloon 120 enters into a more efficient operating range, where less pressure is required to generate the large strains that are afforded by hydraulic/pneumatic actuation. Hence, in this embodiment, the actuator 130 may improve the efficiency of the balloon 120. A similar effect may be achieved where the actuator 130 is provided at an outer surface of the balloon 120, in which case the actuator 130 may be expanded while the balloon is in its fully crimped position, then contracted, followed by expansion of the balloon 120.

Figure 2A:
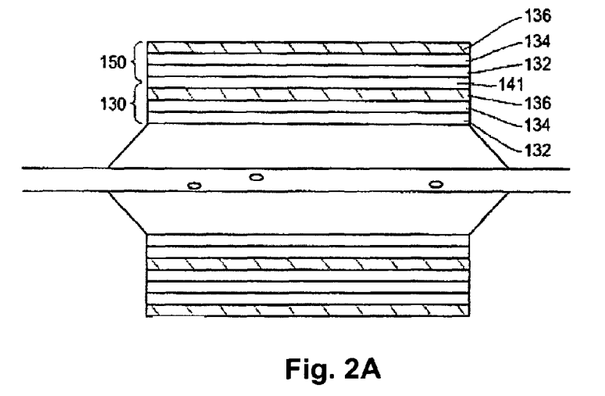
FIGS. 2A and 2B are schematic cross-sectional longitudinal and lateral views, respectively, of a balloon assembly having actuators on its outer surface, which are depicted in a contracted or non-actuated state, in accordance with an embodiment of the present invention.
Figure 2B:
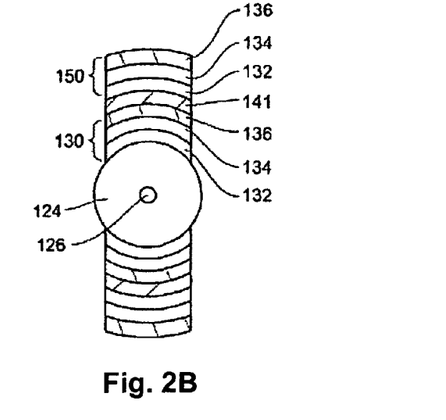
Figure 2C:
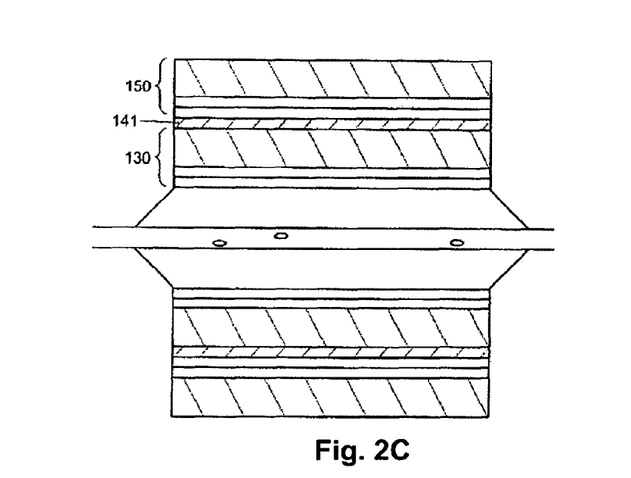
FIGS. 2C and 2D are the views of FIGS. 2A and 2B, respectively, in which the actuators are depicted in an expanded or actuated state.
Figure 2D:
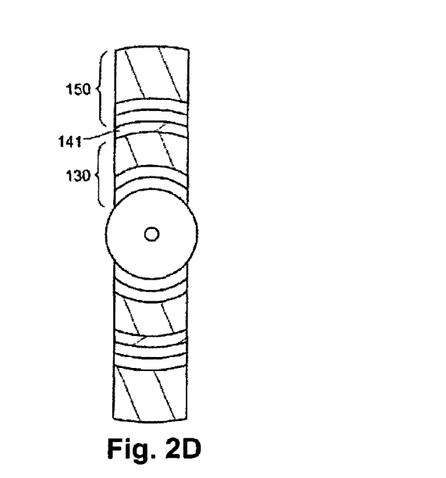

As discussed below, greater dimensional changes may be achieved in various ways, including using thicker electrodes (i.e., thicker particle-containing conductive regions) or by stacking multiple electrodes (e.g., by using multiple actuators). For example, FIGS. 2A and 2B are schematic partial longitudinal and lateral sectional views of a medical device, in a non-activated state, in which multiple actuators are stacked. FIGS. 2C and 2D, on the other hand, show the same views with the actuators 130, 150 in an activated state.

More specifically, theses drawings show an embodiment similar to that illustrated in FIGS. 1A-1D, except that the medical device comprises one or more actuator regions, each containing a second actuator 150 surrounding a first actuator 130. The first and second actuators 130, 150 may be separated by a partition 141. The partition 141 may comprise an insulator or an intervening separator. An insulator may comprise, for example, a ceramic or a non-conductive or poorly conductive polymer region (e.g., latex, rubber, silicon rubber, PEBAX, urethane, PELOTHANE, TECOTHANE, polyester isobutyl styrene, epoxy, thermoplastic elastomer, etc.). Examples of separators are described below.

In the embodiment shown in FIGS. 2A-D, the first and second actuators 130, 150 have the same orientation (i.e., the first electrode 132 is beneath the second electrode 136). In other embodiments, at least one orientation is reversed.

Where the orientation of the inner actuator 130 is reversed, a single first electrode 132 may be employed between two second electrodes 136.

In embodiments such as that shown in FIGS. 2A-D, the actuators 130, 150 may be operatively associated with a power source so that the actuators may be activated independently or collectively.

Any number of actuators may be stacked on one another, with FIGS. 2A-D depicting two stacked actuators for illustrative purposes only. Stacked actuator arrangements such as those shown in respect to the balloon catheter shown may also be employed in other medical devices for which actuation expansion is desired.

Actuators in accordance with the present invention, including those illustrated in FIGS. 1A-1D and 2A-2D, may be formed using a variety of techniques. As one specific example, a series of successive deposition steps, including electrochemical deposition, chemical vapor deposition, and/or physical vapor deposition steps, may be employed in which first electrode 132, separator 134, second electrode 136 and diamond-like coating, are deposited over a permanent or removable underlying substrate.

As another specific example, the components of the actuator 130, including first electrode 132, separator 134, and second electrode 136 may be pressed together at elevated temperature (e.g., between 130° C. and 150° C.) to create a robust structure. The diamond-like coating may be provided on the second electrode 136 either before or after pressing. The layers of the actuator may be hot-pressed together before or after applying the actuator to a surface 122 of the balloon 120. In some embodiments, during assembly, polymer components of the actuator 130 (e.g., the separator material) may be compressed near the melting temperatures of the polymer components to create a more robust interface.

Methods for connecting a preformed actuator 130 to the device (e.g., to balloon 120) include used of adhesives and outer elastic sheaths. Examples of adhesives include, for example, cyanoacrylic adhesives, polyurethane adhesives, and UV curable adhesives, among many others. The actuator may also be sewn to the balloon 120, attached with clamps, and so forth. The actuator 130 or components thereof may be molded in the shape of a particular medical device in some embodiments.

An actuator (with diamond-like coating) for use in the present invention, as well as in various other applications requiring an electrochemical actuator, including a method of forming the same, will now be discussed in conjunction with FIGS. 3A-3D. Turning first to FIG. 3B, a particle-containing conductive region 336 is provided as shown. If desired a conductor 344 (e.g., a metal wire or ribbon) may be embedded within the conductive region 336. For example, the conductor 344 may be placed between two or more carbon-nanoparticle-containing sheets (see, e.g., FIG. 7), which are then laminated (e.g., by hot pressing) to form a carbon-particle-containing conductive region 336, within which conductor 344 is embedded.

In a subsequent step, top and bottom surfaces of the conductive region 336 are provided with a diamond-like coating 336$d$, for example, using techniques such as those described below. The resulting structure is illustrated in FIG. 3C. Note that the diamond-like coating 336$d$ that is applied to the particle-containing region 336 is typically very thin (i.e., thinner than the dimensions of the particles making up the particle-containing regions). Consequently, the texture and porosity of the particle-containing region 336 is commonly at least partially preserved after application of the diamond-like coating 336$d$. Moreover, techniques for forming diamond-like coatings are typically line-of-sight, vacuum-based techniques. As a result, the diamond-like coating 336$d$ generally does not deeply penetrate the underlying particle-containing region 336.

Note that the conductive region 336 may be treated to improve conductivity, for example, using the techniques described below, either before or after application of the diamond-like coating 336$d$.

Figure 3A:
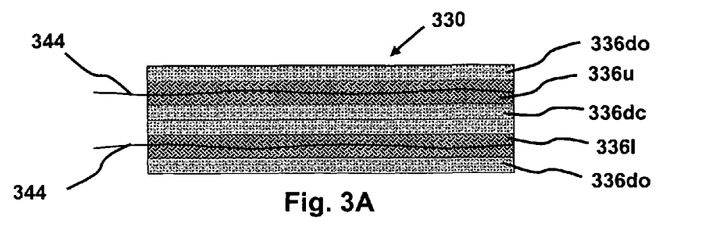
FIG. 3A is a schematic side view of an actuator, in accordance with an embodiment of the present invention.
Figure 3B:
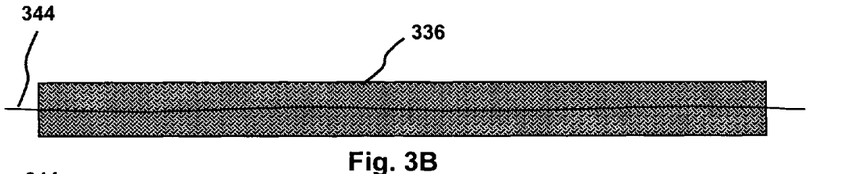
FIGS. 3B and 3C are schematic side views, illustrating a process for making the actuator of FIG. 3A.
Figure 3C:
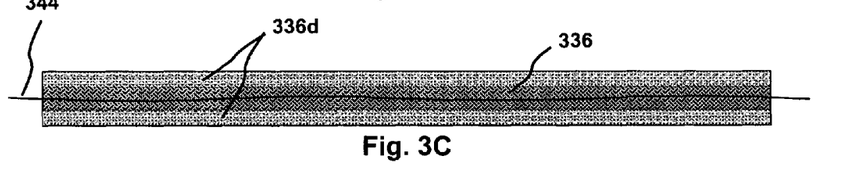

The structure of FIG. 3C is then folded and the region containing the crease is removed (e.g., by cutting the folded structure at the crease), thereby providing the structure of FIG. 3A. Being porous, this structure may be saturated with an electrolytic fluid such as those described elsewhere herein.

At this point, construction of the electrochemical actuator is essentially complete. Being porous, the upper and lower conductive regions, 336$u$ and 336$l$, may function as electrodes during various electrochemical reactions. Moreover, because they are provided with non-conductive surface, the porous central and outer diamond-like coated regions 336$dc$ and 336$do$ will not participate in these electrochemical reactions. Consequently, gas bubble formation will not occur and loss of gas at the outer surfaces may be reduced or eliminated as described above. Also, because the central diamond-like coated region 336$dc$ (which is actually two adjacent diamond-like coated regions) is porous and has a non-conductive surface, it may function as a separator. The conductors 344 facilitate electrical contact between a source of electrical potential and the upper and lower conductive regions 336$u$ and 336$l$, respectively.

Figure 3D:
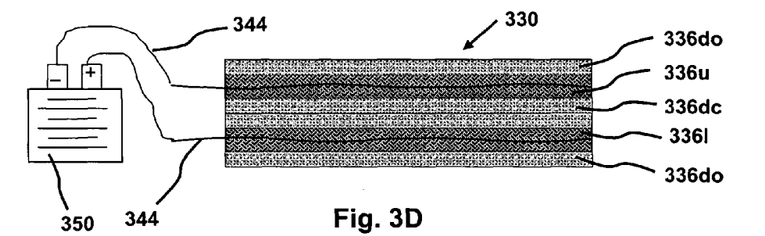
FIGS. 3D and 3E are schematic side views, illustrating the operation of the actuator of FIG. 3A.
Figure 3E:
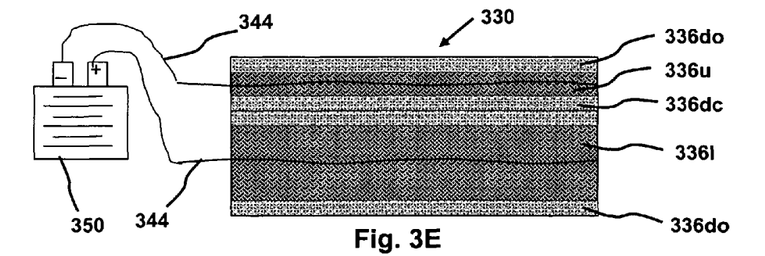

Referring now to FIG. 3D, the actuator 330 of FIG. 3D may be connected to a source of electrical potential such as a battery 350. Assuming that the battery 350 provides a sufficient voltage, then gas bubbles will be produced at the electrode 336$l$ expanding the actuator 330 as seen in FIG. 3E. If desired the polarity may be reversed to return the actuator to the non-expanded state like that of FIG. 3D.

Particles for use in particle-containing regions in accordance with the present invention may be comprised of a variety of materials, including organic and inorganic materials. In certain embodiments, inorganic materials may be preferred as they are frequently stable under the conditions associated with the application of a diamond-like coating. Inorganic materials include metallic materials (e.g., metals and metal alloys) and non-metallic materials (e.g., carbon and semiconductors, glasses, ceramics and various other materials, including a variety of metal- and non-metal-oxides, various metal- and non-metal-nitrides, carbides, borides, phosphates, silicates, and sulfides, among others).

Specific examples of metallic inorganic materials may be selected, for example, from metals (e.g., biostable metals such as gold, platinum, palladium, iridium, osmium, rhodium, titanium, tantalum, tungsten, and ruthenium, and bioresorbable metals such as magnesium), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), and alloys comprising cobalt, chromium, tungsten and nickel (e.g., L605), and alloys comprising nickel and chromium (e.g., inconel alloys).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; carbon-based, ceramic-like carbon materials such as carbon nitrides, and silicate particles including monomeric silicates, polyhedral oligomeric silsesquioxanes (POSS), and clays. Carbon particles are particularly beneficial for certain embodiments of the invention. However, it should be kept in mind that other particulate materials and regions may be used as well.

By "carbon particles" is meant particles that contain carbon, typically containing 50 mol % to 75 mol % to 90 mol % to 95 mol % to 99 mol % or more carbon atoms. Carbon particles for use in the carbon-particle-containing regions of the present invention may take on a variety of shapes, including spheres, polyhedral (e.g., fullerenes), solid cylinders (e.g., carbon fibers), tubes (e.g., carbon nanotubes), plates (e.g., graphite sheets) as well as other regular and irregular shapes.

Carbon particles for use in the invention may vary widely in size. In many embodiments, their smallest dimensions (e.g., the thickness for plates, the diameter for spheres, regular polyhedrons, fibers and tubes, etc.) are less than 10 micrometers (e.g., ranging from 0.5 nm to 1 nm to 10 nm to 100 nm to 1 micrometer to 10 micrometers), whereas additional dimensions (e.g., the width for plates, and the length for fibers and tubes) may be of the same order of magnitude or much larger (e.g., ranging from 0.5 nm to 1 nm to 10 nm to 100 nm to 1 micrometer to 10 micrometers to 100 micrometers to 1000 micrometers or even more).

Particularly beneficial carbon particles are those that comprise molecular carbon that is predominantly in $sp^2$ hybridized form (i.e., structures in which the carbon atoms are predominantly connected to three other carbon atoms within a lattice structure, sometimes referred to as a "grapheme carbon lattice"). Examples of carbon particles that predominantly comprise carbon in $sp^2$ hybridized form include graphite, fullerenes (also called "buckyballs") and carbon nanotubes. Graphite molecules contain planar sheets of $sp^2$ hybridized carbon, whereas fullerenes and carbon nanotubes contain curved sheets of $sp^2$ hybridized carbon in the form of hollow polyhedral (e.g., "Bucky balls") and tubes, respectively. Fullerenes and carbon nanotubes may be thought of as sheets of graphite that are shaped into polyhedral and tubes and, in fact, may be made, among other techniques, by directing a laser at a graphite surface, causing some of the sheets to be displaced from the graphite, which subsequently react to form fullerenes and/or nanotubes.

In certain embodiments of the invention, the carbon-particle-containing regions contain carbon nanotubes, typically 50 wt % to 75 wt % to 90 wt % to 95 wt % to 99 wt % or more carbon nanotubes. Examples of carbon nanotubes include single-wall carbon nanotubes and multi-wall carbon nanotubes (which term embraces so-called "few-wall" carbon nanotubes). Specific examples of nanotubes include single wall carbon nanotubes (SWNTs), which have inner diameters typically ranging from 0.25 nanometer to 0.5 nanometer to 1 nanometer to 2.5 nanometers to 5 nanometers, and lengths up to 100 micrometers, for example, lengths ranging from 10 nanometers to 100 nanometers to 1 micron (μm) to 10 microns to 100 microns, and multi-wall carbon nanotubes, which have inner diameters typically ranging from 2.5 nanometers to 5 nanometers to 10 nanometers, outer diameters of 5 nanometers to 10 nanometers to 25 nanometers to 50 nanometers, and lengths up to 100 micrometers, for example, lengths ranging from 10 nanometers to 100 nanometers to 1 micron (μm) to 10 microns to 100 microns.

SWNTs are particularly preferred for many embodiments of the present invention, including those where a conductive particle-containing region is desired. At present, the purest SWNTs are produced by pulsed laser vaporization of carbon that contains metal catalysts such as nickel and cobalt. Fullerenes are known to form when the carbon is vaporized, mixes with an inert gas, and then slowly condenses. The presence of a metal catalyst, however, is known to form SWNTs. SWNTs are generally considered to be individual molecules, yet as noted above, they may grow to be microns in length. SWNTs may also be produced by other processes such as arc discharge processes.

Regardless of the production technique, after formation, SWNTs are typically purified to remove impurities such as amorphous carbon and residual metal catalysts, for example, by exposure to $NHO_3$ or $HNO_3/H_2SO_4$, followed by rinsing, drying, and subsequent oxidation at high temperatures. A specific technique for providing SWNTs with >99.98 wt % purity (as measured by ICP analysis) is described in the Oak Ridge National Laboratory, Laboratory Directed Research and Development Program, Fy 2003, Annual Report. SWNTs are also commercially available as aqueous suspensions.

Regardless of the specific carbon particles selected, the carbon-particle-containing regions for use in the present invention will typically comprise 50 wt % to 75 wt % to 90 wt % to 95 wt % to 99 wt % or more carbon particles.

Carbon-particle-containing regions for use in the present invention may have various desirable traits, including non-planar surface topography, porosity, and conductivity. For example, as noted above carbon nanotube materials have been shown to be an ideal matrix for endothelial cell growth, which is likely due, at least in part, to the nanostructure and porosity of such materials. Porosity allows for free flow of therapeutic agents, including growth factors and nutrients, and waste products.

Where the particle-containing regions are conductive they may also have the ability to expand substantially under certain conditions, as discussed further below. Macroscopic electrical conductivities typically employed for this and other purposes are generally greater than about $1 \times 10^3$ Siemens/meter (S/m), more generally ranging from $1 \times 10^4$ S/m to $5 \times 10^6$ S/m. Conductivities may be measured, for example, using a four probe measurement.

Particle-containing regions for use in conjunction with the present invention may be formed using any suitable method for forming such regions. For example, carbon-particle-containing regions may be formed by suspending carbon particles (e.g., SWNTs) in an appropriate fluid (e.g., water, one or more organic solvents such as toluene or chloroform, or a mixture of water and organic solvent), which may contain further optional agents as desired such as surfactants (e.g., Triton X-100, an alkylaryl polyether alcohol or octyl phenol ethoxylate). SWNT suspensions are commercially available, for example, from Zyvex, Richardson, Tex., USA and Rice University, Houston, Tex., USA. The suspension is then brought into contact with a substrate of choice to form a carbon-particle-containing region.

In some embodiments, a particle-containing region is formed on an underlying substrate, which is (or becomes) part of the medical device (i.e., a permanent substrate). In other embodiments, the particle-containing region is formed on a temporary substrate, from which it is subsequently removed (e.g., by separating the particle-containing region from the substrate or by sacrificing the substrate by a process such as dissolution, melting, etc.).

As a specific example, SWNT suspensions may be sprayed onto desired substrates (e.g., using single or multi-orifice spray heads, ink jet, etc.) and the liquid allowed to evaporate (e.g., at elevated temperatures), thereby forming SWNT layers. The density of the SWNT layers may be varied, for example, by adjusting the spray duration, the SWNT concentration, the nozzle pressure, and so forth, which may cause a variation, for example, in the diameter of bundles (or so-called "ropes") of SWNTs that are formed. Alternatively, substrates may be dipped into suspensions of SWNTs to form SWNT layers. For high density packing of the SWNTs, an additional step may be taken by compressing the SWNTs.

As another specific example, carbon particle suspensions (e.g., SWNT suspensions) may be vacuum-filtered to produce freestanding carbon-particle-containing sheets, for instance, so-called "carbon nanotube paper" or "bucky paper," which contains highly entangled nanotube ropes, as described, for example, in U.S. Patent Appln. Pub. No. 2004/0138733 and in G. M. Spinks, et al., "Pneumatic Actuator Response from Carbon Nanotube Sheets," Materials Research Society Symposium Proceedings, Vol. 706, Making Functional Materials and Nanotubes (Materials Research Society, Pittsburgh, 2002) pp. Z9.22.1-6, the disclosures of each of which are hereby incorporated by reference. A typical nanotube paper produced by such a process is between 15 and 35 microns thick, has a bulk density of 0.3 to 0.4 grams per cubic centimeter, and has a four point conductivity on the order of 5,000 S/cm (e.g., 1,000 to 10,000 S/cm). The nanotubes commonly aggregate spontaneously into bundles or "ropes" of approximately 10 nanometers in diameter and many microns in length. The nanotube paper may then be peeled from the filter to produce a freestanding film. Alternatively, a filter material may be employed that is subsequently sacrificed (e.g., by dissolution, evaporation, combustion, etc.).

Other processes for producing carbon nanotube paper are described, for example, in A. G. Rinzler, J. Liu, et al., "Large scale purification of single-wall carbon nanotubes: process, product and characterization," *Applied Physics A*, A67, 29-37 (1998), K. D. Ausman, et al., "Organic Solvent Dispersions of Single-Walled Carbon Nanotubes: Towards Solutions of Pristine Nanotubes," *J Physical Chem.*, 104 (38):8911-8915 (2000), and T. V. Sreekumar, et al., "Single-Wall Carbon Nanotube Films," *Chem. Mater.*, 15:175-178 (2003), each of which are also expressly incorporated herein by reference. Commercially available carbon nanotube layers may also be employed. Once formed or obtained, such carbon-particle-containing regions may be adhered to a permanent substrate of choice.

Alternatively, a permanent substrate (e.g., a medical device or medical device component, a conductive or non-conductive mesh, etc.) may be positioned on top of a filter whereby at least part of the substrate is embedded within the particle-containing region at the same time as the region is formed. For instance, a tubular filter may be used in which one initially produces a first particle-containing layer on the inside of the tubular filter (e.g., using centrifugal force), after which one positions a tubular medical device (a stent, for example) within this ensemble, with close contact being established between the device and the particle-containing layer. One then repeats the process of making the particle-containing layer to create a second layer, such that the device becomes encapsulated between the first and second layers.

In case of a stent having multiple struts or wires, the struts or wires are surrounded in whole or part by the particle-containing material. Many stent designs may also be readily expanded in the tubular filter and thus brought into close contact with the first layer.

Figure 7:
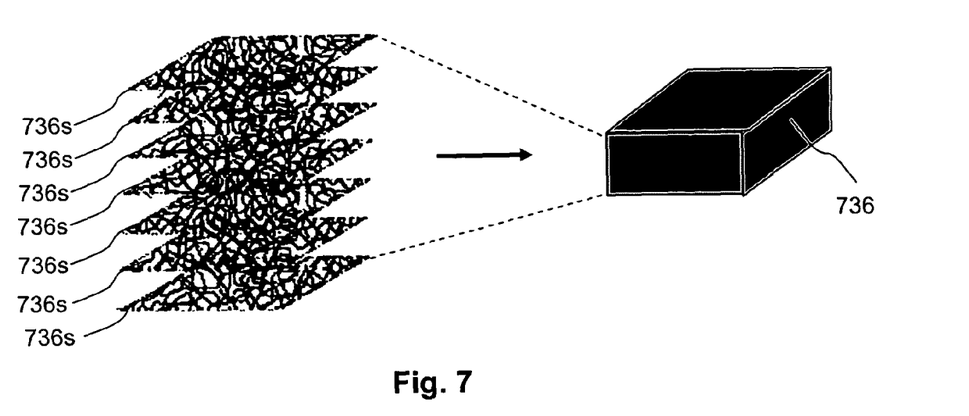
FIG. 7 is a schematic view of a process of forming a carbon-particle-containing region from carbon nanotube sheets.

In certain embodiments of the invention, multiple particle-containing layers are laminated to form a single particle-containing region. For example, as schematically illustrated in FIG. 7, multiple carbon-particle-containing sheets such as nanotube sheets $736s$ may be laminated into a single carbon-particle-containing region $736$. Being formed from carbon nanotubes, the sheets $736s$ have an intrinsic porosity which is conveyed to the laminate $736$. For example, the sheets $736s$ may be stacked and pressed together at elevated temperature to create the laminate $736$. The void space in the laminate $736$ may be increased by providing sheets $736s$ with a non-planar surface, for example, with a corrugated or indented surface. Such sheets may be made, for example, using a filter with corrugations or protrusions or indentations using the above described techniques, for example.

Where conductive carbon-particle-containing regions are employed, various measures may be employed to increase the conductivity of the same. For example, the carbon-particle-containing regions may be irradiated with a dose of radiation (e.g., gamma irradiation) that is sufficient to increase the conductivity. This may be done either before or after providing the carbon-particle-containing region with a diamond-like coating (discussed below in more detail). As another example, the carbon-particle-containing region may be chemically treated under conditions sufficient to increase conductivity, likewise either before or after providing the region with a diamond-like coating.

In a specific example, a carbon-nanotube-containing region is irradiated with approximately 170 kGy of gamma radiation as described in Skakalova, V., et al. "Gamma-irradiated and functionalized single wall nanotubes." *Diamond Relat. Mater.* 13(2): 296-8 (2004). A diamond-like coating is then applied, for example, as described below. This structure may then be treated with thionyl chloride, $SOCl_2$, as described in Urszula Dettlaff-Weglikowska et al., Abstract HH 13.36 "Enhancement of Conductivity of Bucky Paper by Chemical Modification" Symposium HH, Functional Carbon Nanotubes, 2004 MRS Fall Meeting, Boston Mass., USA. As noted above, diamond-like coatings are typically very thin. Consequently, the texture and porosity of the underlying carbon-nanotube-containing region is typically at least partially preserved, allowing the $SOCl_2$ to react with the defects on the carbon nanotubes in the interior of the structure. In addition to improving conductivity, functionalization with $SOCl_2$ is also believed to improve bubble retention within the carbon-particle-containing region—a desirable trait where the carbon-particle-containing region is used as an actuator.

As used herein a "diamond-like coating" is one that, like diamond, is both hard and non-conductive. As used herein a "non-conductive" material is one that has a volume resistivity in excess of 1 ohm-cm. Examples of diamond-like coatings include boron nitride coatings, boron carbide coatings, and diamond-like carbon coatings, among others.

Analogous to carbon, boron nitride forms both hard, diamond-like $sp^3$-bonded phases and softer, graphite-like $sp^2$-bonded phases. The cubic phase of boron nitride, or cBN, is reported to be second in hardness only to diamond, with a Vickers hardness of about 5000 kg $mm^{-2}$ (49 GPa). Resistivities are on the order of $10^9$ and higher have been reported to for predominantly cBN films. BN films with a high (>85%) percentage of the cubic phase may be deposited by a variety of deposition techniques (e.g., vapor deposition, pulsed laser deposition, etc.), which may employ energetic particle bombardment. For further information, see, e.g., P. B. Mirkarimi et al., "Review of advances in cubic boron nitride film synthesis," *Materials Science and Engineering*, R21 (1997) 47-100.

Boron carbide ($B_4C$) is the third hardest material after diamond and cBN, with a highest Vickers hardness (VH) similar to that of cBN at around 5000 kg mm$^{-2}$ (49 GPa). Volume resistivity is on the order of $10^2$ Ohm-cm or less. Techniques for forming boron carbide layers include pulsed laser deposition, chemical vapor deposition (CVD), magnetron sputtering, and plasma spraying, among others. For further information, see, e.g., S. Aoqui et al., "Preparation of boron carbide thin film by pulsed KrF excimer laser deposition process," *Thin Solid Films* 407 (2002) 126-131.

"Diamond-like carbon coating" is a generic term for a mixture of $sp^2$ (as in graphite) and $sp^3$ (as in diamond) bonded carbon. It is generally described as hard, amorphous, and chemically inert. Diamond-like carbon coatings are known to be biocompatible and they are relatively non-conductive, with electrical resistivities of $10^9$ Ohm-cm and higher being typical. Typical diamond-like carbon coatings contain 80 mol % to 90 mol % to 95 mol % or more carbon atoms. Consequently, these coatings may contain other elements, introduced either unintentionally (e.g., as impurities) or intentionally (e.g., as dopants).

Properties of diamond-like carbon coatings generally vary with the ratio of $sp^3$ to $sp^2$ bonding. For example, a variation in the $sp^3$ fraction (i.e., the number of $sp^3$ carbons÷(the number of sp carbons+$sp^2$ carbons)) from 10% to 80% has been reported to correspond to a change in hardness from about 10 GPa to about 90 GPa. Preferably, the diamond-like carbon coatings comprise an $sp^3$ fraction of 50% to 60% to 70% to 80% or more. In this regard, the term "tetrahedral amorphous carbon" (ta-C) is sometimes used to refer to diamond-like carbon materials with a high degree of $sp^3$ bonding (e.g., greater than or equal 80%, typically 80-90%).

The diamond-like coating renders the underlying particle-containing region highly wear resistant. Furthermore, diamond-like coatings may be quite thin, ranging, for example, from 5 nm up to several micrometers, more typically from 10 nm to 100 nm. Thus, these coatings generally at least partially preserve the topography of the underlying particle-containing region.

Diamond-like coatings may be formed using a number of deposition techniques, including laser plasma deposition (e.g., pulsed laser deposition), ion beam deposition, magnetron sputtering, ion sputtering, plasma activated chemical vapor deposition, and ion plating. These processes may involve, for example, deposition from a beam/plume of energized (e.g., 10-500 eV) ions.

For instance, the deposition of amorphous diamond coatings on SWNTs is described in A. A. Puretzky et al., "Synthesis and characterization of single-wall carbon nanotube-amorphous diamond thin-film composites," *Applied Physics Letters*, Vol. 81, No. 11, 9 Sep. 2002. Specifically, pulsed laser deposition (PLD) of tetragonally-coordinated amorphous carbon is performed in vacuum (~$10^{-5}$ Torr) using a pyrolytic graphite target irradiated at 193-nm with an ArF-excimer laser (energy density F~1.8 J/cm$^2$), which generates a plume that contains carbon ions having kinetic energies up to 100 eV.

Diamond-like coatings have also been applied to polymers. In this regard, Mark S. Hammond and A. Wesley Moorehead of SI Diamond Technology, Inc. have reported the use of a diamond like carbon coating material, Amorphic Diamond™, which comprises nodules of carbon that have the molecular/crystalline structure of diamond, with sizes of 100 to 200 nm, densely and uniformly packed in a net of amorphous carbon polytypes. This material is reported to be able to withstand flexure and shock without cracking, and it can be applied to plastic, polymer, metal, and ceramic substrates.

One could introduce a polymer inside of a carbon paper structure after a diamond like coating has been applied, for example, by dip coating or spraying a dissolved polymer, polymerizing a monomer in a plasma process, by applying a thin polymer film onto the carbon paper structure and melting the polymer into the top layer of the paper.

The unique properties of carbon-particle-containing regions with diamond-like coatings (also referred to herein as a "diamond-coated carbon-particle-containing regions"), including their flexibility, wear resistance, surface texture and porosity, as well as their conductivity characteristics, render them useful for a broad range of medical device applications.

Figures 4A, 4B:
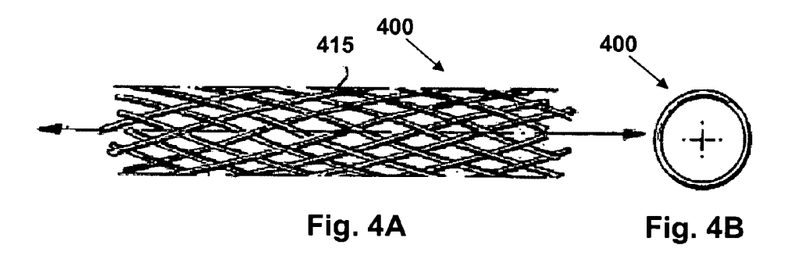
FIGS. 4A and 4B are schematic longitudinal and end views, respectively, of a stent.

Specific embodiments of medical devices in accordance with the present invention will now be described in conjunction with FIGS. 4A and 4B, which are schematic, longitudinal and end views, respectively, of a stent 400, which is made up of a plurality of helically woven coated wires 415. Although a woven stent is illustrated, the invention is applicable to other stent designs, including laser cut stent designs, among others.

Figure 4C:
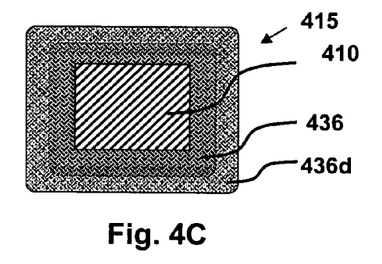
FIGS. 4C-4E are cross-sectional views of a coated wire of the stent of FIGS. 4A and 4B, in accordance with three different embodiments of the present invention.

In one embodiment, illustrated in FIG. 4C, a cross-sectional view of the coated wires 415 reveals a metallic (e.g., stainless steel, nitinol, etc.) or non-metallic (e.g., polymer, ceramic, etc.) wire core 410, covered with a particle-containing layer 436 having a diamond-like coating 436*d*. The wire core 410 acts as a permanent substrate for the diamond-coated particle-containing layer 436,436*d*. Techniques for providing the diamond-coated layer 436,436*d* are described above and include spraying with or dipping in a carbon particle suspension to form the carbon-particle-containing layer 436, followed by deposition of the diamond-like coating 436*d*, among other techniques. The particle-containing layer 436, the diamond-like coating 436*d*, or both, may be provided over the wire core 410 before the stent 400 is formed (e.g., by weaving/braiding the wires), or they may both be formed after the stent 400 is formed.

Although the substrate in this particular embodiment is a stent wire core 410, clearly the diamond-coated layer 436, 436*d* may be applied to practically any suitable medical device substrate, including substrates corresponding to all or a portion of the various medical devices described above.

As indicated above, diamond-coated particle-containing regions are desirable for a wide range of medical devices because, among other things, they may be biocompatible, wear resistant, flexible, porous, and have a surface topography that may influence cell growth.

Where porous, the diamond-coated particle-containing regions are capable of acting as reservoirs or metering membranes for therapeutic agents. For example, the therapeutic agent may be provided beneath the diamond-coated particle-containing regions, within the non-diamond-coated portions of the particle-containing regions, and/or within the diamond-coated portions of the particle-containing regions.

Numerous therapeutic agents which may be disposed beneath or within the diamond-coated particle-containing layers of present invention are described in paragraphs [0040] to [0046] of commonly assigned U.S. Patent Application Pub. No. 2003/0236514, the entire disclosure of which is hereby incorporated by reference. A few specific examples of therapeutic agents for use in conjunction with medical devices in accordance with the present invention, including drug eluting catheters and stents, include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein among others.

Hence, one or more therapeutic agents may be provided within (or beneath) the diamond-coated particle-containing layers of the present invention, including within the diamond-coated particle-containing layer 436, 436d of FIG. 4C.

Figure 4D:
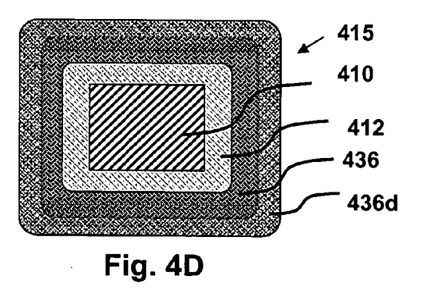

The embodiment illustrated in cross-section in FIG. 4D is similar to that of FIG. 4C described above, except that a therapeutic-agent-containing region 412 is supplied between the wire core 410 and the particle-containing region 436. The therapeutic agent may be present in substantially pure form or may be present within a carrier material, for example, a polymer or polymer blend. Suitable polymers and polymer blends may be selected, for example, from those listed in paragraph [0054] of U.S. Patent Application Pub. No. 2003/0236514. This document also describes various ways of providing therapeutic-agent-containing regions over a substrate, including thermoplastic and solvent-based processing techniques. Once a core 410 with therapeutic-agent-containing region 412 is provided, then a particle-containing layer 436 and a diamond-like coating 436d may be created over the therapeutic-agent-containing region 412, for example, using techniques such as those described above.

In certain embodiments, the following materials may be utilized for the device illustrated in FIG. 4D: an electrically conductive wire core 410, such as metal or metal-alloy wire, a therapeutic-agent-containing region 412 that (i) contains containing a mobile, charged therapeutic agent (e.g., either a therapeutic agent that is inherently charged, or one that is modified to comprise a charged group) and (ii) is sufficiently non-conductive to prevent an electrical short from occurring between the conductive wire core 410 and a conductive particle-containing layer 436 at voltages effective to promote migration of the charged therapeutic agent. In these embodiments, the wire core 410 and the conductive particle-containing layer 436 are connected to a source of electrical potential, which creates an electric field across the therapeutic-agent-containing region 412. Consequently, the charged therapeutic agent is driven either toward the wire core 410 or toward the conductive particle-containing layer 436, depending on the bias that is applied. In this way, therapeutic agent delivery may be assisted, hindered, or hindered and then assisted, as desired. The power source may supply a constant voltage, a pulsed voltage or both. Where a pulsed voltage of sufficient magnitude is applied, electroporation of surrounding cells/tissue may be achieved. Although this above embodiment concerns a stent formed from conductive wires, the same effect may be achieved with essentially any medical device, so long as the therapeutic-agent-containing region is provided between a conductive member and a conductive particle-containing region.

Figure 4E:
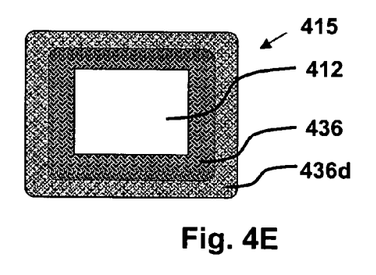

In accordance with other embodiments, the core 410 illustrated in FIG. 4C may be made out of a sacrificial material. This structure may then be provided with a particle-containing layer 436 and a diamond-like coating 436d, after which the core 410 may be dissolved and then replaced by a therapeutic-agent containing region 412 (see, e.g., FIG. 4E). This may be especially useful where a therapeutic agent is employed that can not survive the diamond-like coating process conditions.

In still other embodiments of the invention, diamond-coated particle-containing regions in accordance with the invention are used to encapsulate pockets of therapeutic agents within one or more apertures (e.g., mechanically or laser cut apertures), which apertures may extend partially or completely through a medical device surface.

Figure 5A:
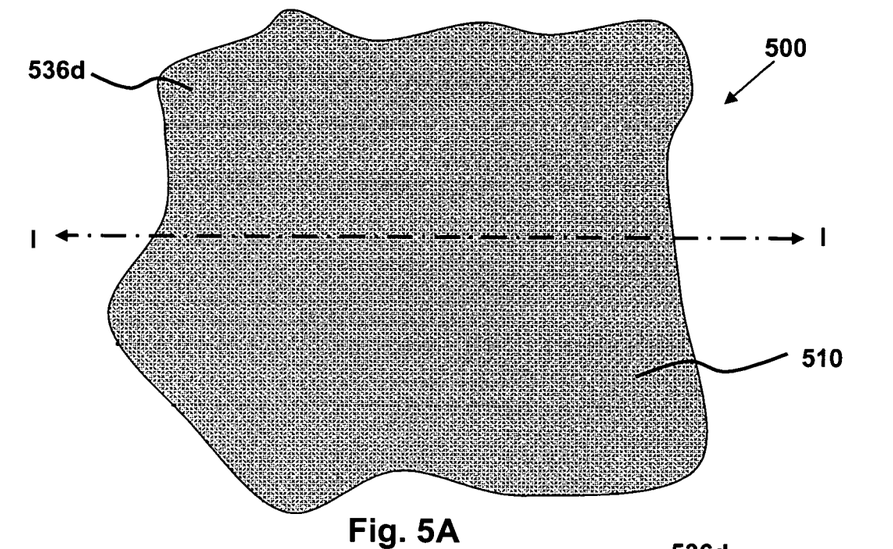
FIG. 5A is a schematic, partial longitudinal view of a stent wall.

For example, FIG. 5A is a schematic, partial longitudinal view of a stent wall 500, which is covered with at least one diamond-coated particle-containing region. The diamond-like coating 536d is illustrated in FIG. 5A, along with the underlying stent structure 510 (depicted by dashed/hidden lines).

Figure 5B:
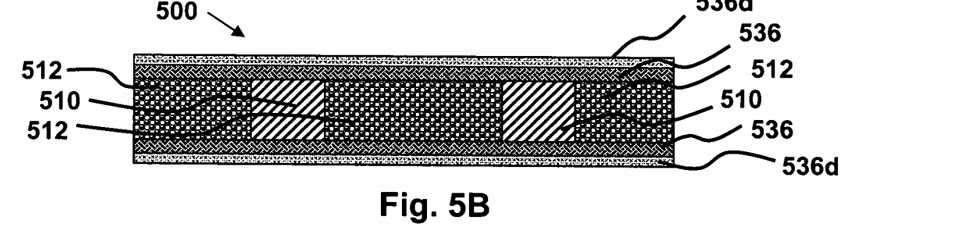
FIG. 5B is a cross-sectional view of the stent wall illustrated in FIG. 5A, taken along line I-I, in accordance with an embodiment of the present invention.

FIG. 5B is a cross-sectional view of the stent wall 500 illustrated in FIG. 5A, taken along line I-I, in accordance with one embodiment of the invention. FIG. 5B shows stent struts 510, which may be formed, for example, from any suitable metallic or non-metallic material. Between the stent struts 510 are provided various therapeutic-agent-containing regions 512. The therapeutic agent may be present in the regions 512 in substantially pure form or within a carrier material. Examples of suitable therapeutic agents and carrier materials are set forth above. The struts 501 and therapeutic-agent-containing regions 512 are sandwiched between two particle-containing layers 536, each having a diamond-like coating 536d, which correspond to the inner and outer surfaces of the stent wall 500.

Figure 5C:
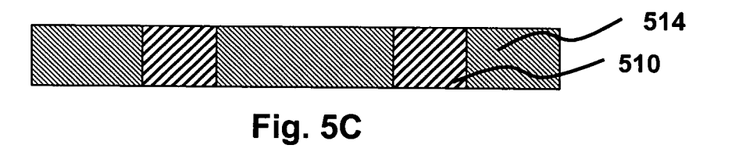
FIGS. 5C-5E are cross-sectional views illustrating a process of making the stent wall of FIGS. 5A and 5B.

Numerous techniques are available for forming the structure of FIGS. 5A and 5B. One such method is described in conjunction with FIGS. 5C-5E. For example, in a first step, a removable material 514 is first provided between the struts 510, as illustrated in FIG. 5C. Examples of such removable materials include materials that may be removed by any suitable process such as melting, sublimation, combustion, dissolution or other process which selectively removes the material without destroying other portions of the structure. For instance, in some embodiments, the removable material 514 is made from a material that melts at moderately elevated temperatures (e.g., 60° C.), for instance, dental waxes such as those available from MDL Dental Products, Inc., Seattle, Wash., USA. Other examples of removable material 514 are materials that are essentially insoluble in cold water, but are soluble in hot water. Polyvinyl alcohol (PVOH) is one example of such a material.

Figure 5D:
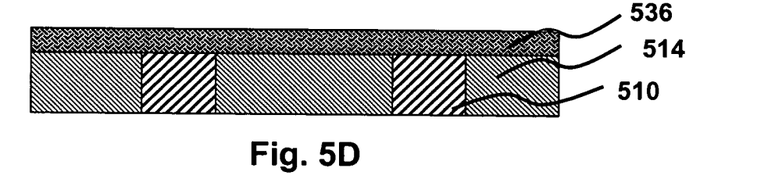
Figure 5E:
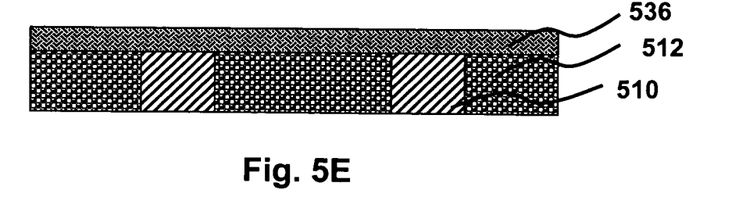

Once the removable material 514 is in place, a particle-containing layer 536 is applied over the structure of FIG. 5C, to produce the structure illustrated in FIG. 5D. Such a layer 536 may be applied as described above, for example, by spraying a carbon nanotube suspension over the structure of FIG. 5C.

The removable material 514 is then removed from the structure of FIG. 5D and replaced with therapeutic-agent-containing regions 512, which may be, for example, made entirely of therapeutic agent or may comprise a therapeutic agent dispersed within another medium. For example a fluid containing one or more dissolved and/or dispersed therapeutic agents and an optional carrier, such as a therapeutic-agent-containing polymer melt, may be applied to fill the recesses created by the removal of removable material 514, followed by solidification of the fluid, and removal of solidified material (if any) from the upper surfaces of the strut 510, resulting in the structure of FIG. 5E. As another example, the voids created by removal of removable material 514 may be filled with a particulate material that consists of or contains the therapeutic agent.

Regardless of how the voids are filled, an additional particle-containing layer 536 is then applied opposite the previously established layer 536, for example, using techniques such as those described above. Finally, the top and bottom particle-containing layers 536 are provided with a diamond-like coating 536d, again using techniques such as those described above, thereby producing a structure in accordance with FIG. 5B.

In other embodiments, for example, where a therapeutic agent is employed that cannot survive the diamond-like coating process conditions, the removable material may be removed and replaced with the therapeutic agent after the formation of the top and bottom particle-containing layers and diamond-like coating.

Figure 6A:
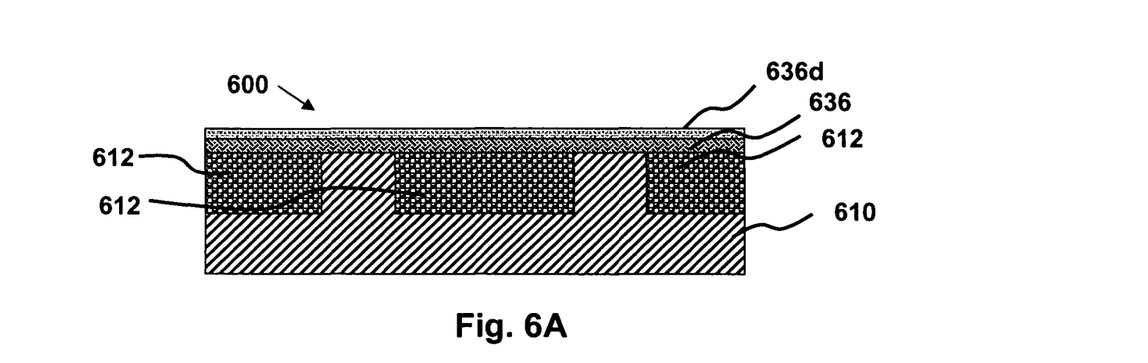
FIG. 6A is a cross-sectional view of the stent wall illustrated in FIG. 5A, taken along line I-I, in accordance with another embodiment of the present invention.

In other embodiments, a medical device is provided which has apertures that do not extend completely through the same. For example, FIG. 6A illustrates an embodiment of the invention analogous to that of FIG. 5B, except that the apertures 610a within the medical device struts 610 do not extend completely through the struts 610. Hence, only a single particle-containing layer 636 with diamond-like coating 636d is required to encapsulate the therapeutic-agent-containing regions 612.

Figure 6B:
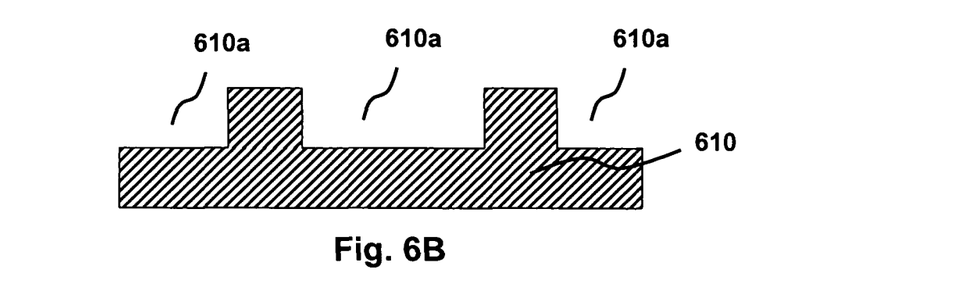
FIGS. 6B and 6C are cross-sectional views illustrating a process of making the stent wall of FIGS. 5A and 6A.
Figure 6C:
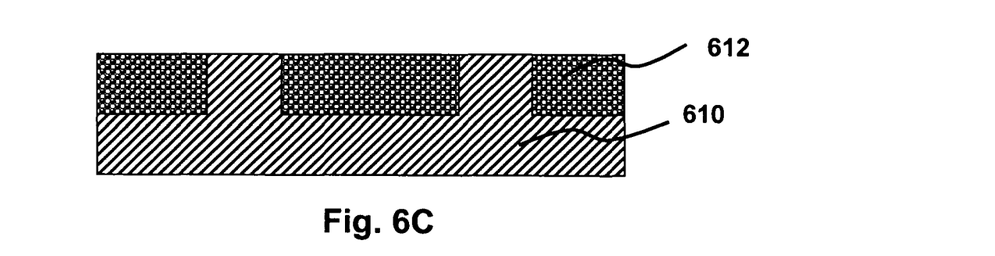

Such a device may be made in a fashion similar to that described in FIGS. 5A-5E. For example, struts 610 having apertures 610a may be provided as illustrated in FIG. 6B. As shown in FIG. 6C, these apertures are then filled with therapeutic-agent-containing regions 612, for example, as described above. Then, a particle-containing layer 636 is applied over the structure of FIG. 6C, followed by deposition of a diamond-like coating 536d, for example, using techniques such as those described above, thereby producing a structure in accordance with FIG. 6A. Also as above, where a therapeutic agent is employed that cannot survive the diamond-like coating process conditions, the removable material may be removed and replaced with the therapeutic agent after the formation of the particle-containing layer and diamond-like coating. As elsewhere herein, despite the fact that the above embodiments concern stent struts having multiple partial or complete apertures, this is for illustrative purposes only and the same result may be achieved with essentially any medical device having a substrate with one or more complete or partial apertures.

In other embodiments, diamond-coated particle-containing regions are used as outer coatings for bioerodible stents made, for example, from a bioerodible polymer or a bioerodible metal, such as magnesium, iron, or their alloys. In this way, a coating is provided which surrounds the bioerodible material while at the same time allowing erosion to proceed. Any particles escaping from the main stent structure during degradation are captured within the coating. As indicated elsewhere herein, therapeutic agents may be provided within the coating, where desired. Where the coating is diamond-coated, carbon-nanotube-containing region, after the stent has completely degraded, one is left with a structure consisting of the carbon nanotubes, some of which are diamond-coated.

As indicated above, certain embodiments of the invention make use of the fact that particle-containing conductive regions like those described herein are known to be useful for purposes of electromechanical actuation, for example, where carbon-particle-containing conductive regions are employed. See, e.g., Spinks et al. above and U.S. Patent Appln. Pub. No. 2004/0138733.

In these embodiments, a power source is used to provide a voltage across at least first and second electrodes, which are in electrically bridged to one another by an electrolyte and supporting medium. In order to prevent shorting, a separator may be provided between the electrodes. For example, with reference to FIGS. 1A-1D, actuator 130 of this device comprises a first electrode 132, a separator 134, and a second electrode 136.

More particularly, the first electrode may comprise any conductive material suitable for functioning as an anode and/or cathode in the electrochemical reactions that take place during the course of activation or de-activation. Examples of conductive materials include suitable members of the following: metals and metal alloys (e.g., gold or platinum, due to their high conductivity, oxidation resistance, and radiopacity, which facilitates visibility of the device during fluoroscopy or the like), carbon-particle-containing conductive materials and conductive polymers, and among many other materials.

The second electrode may comprise a particle-containing conductive region with a diamond-like coating as described herein. For actuators, the thickness of the particle-containing conductive region may vary widely, for example, ranging from 1 to 100 μm. Single or multiple particle-containing conductive regions may be employed in a given electrode, for example, arranged laterally or stacked in order to achieve greater dimensional changes. Greater dimensional changes may also be achieved by stacking multiple actuators.

The separator, where employed, may be selected from various separators known in the electrochemical arts, and is typically formed from a material that serves to prevent the first and second electrodes from shorting, while at the same time allowing transport of charged species between the same, thereby closing the electrical circuit between the electrodes. Examples of separator materials include proton exchange membranes (PEMs). PEMs that may be utilized include, for example, Nafion (which, for example, may comprise a perfluorinated ion-exchange solution), and ionomers such as sulfonated poly(styrene-isobutylene-styrene) (S-SIBS). Nafion products, including membranes and ion-exchange solutions are available from ElectroChem, Inc., Woburn, Mass., USA. Details and use of S-SIBS is provided in "Transport Properties of Triblock Copolymer Ionomer Membranes For Fuels Cells," Y. A. Elabd, et al., 23rd Annual Army Science Conference Oral Paper AO-02 (2002), the disclosure of which is expressly incorporated herein by reference. Other examples of separators include electrical insulators, such as various ceramic materials and polymers (e.g. polyolefin, polyamide, silicone, polyurethane, polyester and poly(vinyl aromatic) homopolymers and copolymers, among many others, for example, TECOTHANE), which provide a way for ions to move through the separator, for example, due to the presence of pores, holes or other openings.

The electrolyte provides mobile charged species (e.g., ions) which move between the first and second electrodes and which may participate in the chemical reactions that occur at the electrodes. Examples of suitable electrolytes include organic and inorganic salts and acids, such as alkali metal halides and alkaline earth metal halides, more preferably alkali metal chlorides, such as potassium chloride or sodium chloride, and acid chlorides such as HCl. The electrolyte may be supported in ionized form within any suitable ion supporting medium, including solids, gels and liquids. Liquids are preferred as supporting media in various embodiments of the invention. Specific examples of liquids suitable for this purpose include, for example, polar organic liquids, water, and mixtures of water and organic liquids.

For mechanical actuation, the electrolyte may provide ions (e.g., chloride ions) that participate in electrochemical reactions that result in bubble formation (e.g., bubbles of oxygen, chlorine, etc.) upon application of a suitable electric potential across the first and second electrodes. These bubbles, in turn, cause expansion of the second electrode.

One will appreciate that the choice of electrolyte and supporting medium will be influenced by whether the actuator is to be open to body fluids or not. For example, diamond-coated particle-containing regions are frequently porous and may therefore allow use of blood plasma or other body fluids to supply both the desired electrolyte (e.g., ions within the blood) and supporting medium (e.g., water).

In other embodiments, the actuator components are not open to the surrounding environment and are therefore provided with an appropriate electrolyte and supporting medium prior to deployment of the device. For example, a sheath may be provided which isolates the actuator components from the outer environment. See, e.g., FIGS. 8A and 8B, described above. The sheath may be manufactured from a variety of materials including, for example, elastomeric polymer materials. For example, sheaths may be manufactured from latex rubber, silicon rubber, polyether polyamide block copolymers such as PEBAX, urethanes such as PELLETHANE and TECOTHANE, polyesters, polyisobutylene-polystyrene block copolymers, and so forth. Of course, a porous elastomeric sheath may be employed if one wishes to use blood plasma or other body fluids as the electrolyte and supporting medium.

The power source employed should be capable of applying a first voltage sufficient for the electrochemical formation of gas bubbles within the particle-containing conductive region(s), and may also be capable of applying a second voltage of opposite polarity from the first voltage that is sufficient to reverse the electrochemical reactions leading to bubble formation. The power source may supply, for example, a constant (direct) or variable (e.g., pulsed) current/voltage. Examples of power sources for supplying direct current include batteries and rectified alternating current sources. Voltages on the order of one volt are sufficient to generate gas within the diamond-coated particle-containing conductive regions.

Without wishing to be bound by theory, it is believed that one or both of the following reactions typically occur during gas bubble formation:

$$2Cl^- \rightarrow Cl_2(g) + 2e^- \quad E_0 = 1.12V \text{(vs. } SCE)$$

$$2H_2O \rightarrow O_2(g) + 4H^+ + 4e^- \quad E_0 = 0.99 \text{ V (vs. } SCE)$$

Gas bubbles are generally observed at the surfaces of the carbon particles within carbon-particle-containing conductive regions. Gas bubble formation causes the carbon particles, or aggregates of the carbon particles (e.g., nanotube "ropes") to move apart, which in turn causes the volume of the conductive region to expand. As a specific example, carbon nanotube layers have been observed to increase in thickness by around 300% (although lesser and greater percentages are also possible), with the length of the layer remaining substantially the same. By reversing the polarity, the reactions may likewise be reversed, causing the carbon-particle-containing layer to shrink. Kinetically, the reactions leading to bubble formation and expansion may occur over a period that is on the order of tens of seconds, whereas the reactions leading to collapse may occur over a period that is on the order of a second.

In general, gas bubbles generated in the interior of the particle-containing regions are trapped within the region and do not escape to any significant degree. However, gas bubbles created at the surface of the conductive region can have a tendency to escape into the surrounding environment, unless preventative steps are taken. In the present invention, formation of gas bubbles at the surface of the particle-containing region is prevented by providing this region with a diamond-like coating. Unlike the underlying conductive region, the diamond-like coating is sufficiently non-conductive to prevent the surface region from functioning as an active electrode region during the electrochemical reactions that result in bubble formation. Consequently, bubbles do not form at the diamond-like coating surface.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising:
   (a) a polymer or metal substrate;
   (b) a particle-containing region on the substrate that forms a layer, said layer comprising particles of one or more materials or particulate forms, said layer including a layer surface, and the particles being particulates having a minimum dimension of at least 0.5 nm and a maximum dimension of 1000 microns or less and comprising carbon particulates,
   (c) said layer being a component of an mechanical actuator system that is configured to electrochemically generate bubbles within the particle-containing region when a voltage is applied, said system further comprising an electrolyte in said particle-containing region, a pair of electrodes and a separator, and
   (d) a porous diamond-like coating layer on the surface of said particle-containing region.

2. The medical device of claim 1, wherein the said particle-containing region comprises carbon nanotubes.

3. The medical device of claim 1, wherein the said particle-containing region comprises single wall carbon nanotubes.

4. The medical device of claim 1, wherein said particle-containing region is formed as a said layer on said substrate from a liquid suspension of carbon-particles.

5. The medical device of claim 1, wherein said particle-containing region is formed as a said layer from two or more sheets, each comprising carbon-particles.

6. The medical device of claim 1, wherein the said particle-containing region is from 1 to 100 μm in thickness.

7. The medical device of claim 1 wherein said device comprises a plurality of layers comprising carbon particles.

8. The medical device of claim 1, wherein said diamond-like coating is a diamond-like carbon coating.

9. The medical device of claim 8, wherein said diamond-like carbon coating contains an $sp^3$ fraction ranging from 60% to 95%.

10. The medical device of claim 8, wherein said diamond-like carbon coating is formed by a pulsed laser deposition technique.

11. The medical device of claim 8, wherein said diamond-like carbon coating ranges from 50 to 100 nm in thickness.

12. The medical device of claim 1, wherein said particle-containing region has a second diamond-like coating layer on an inner surface thereof and said separator comprises said second diamond-like coating.

13. The medical device of claim 1, wherein said device includes a therapeutic agent disposed beneath or within said particle-containing region.

14. The medical device of claim 13, wherein said therapeutic agent selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, and combinations thereof.

15. The medical device of claim 1, wherein at least a portion of said medical device is configured for implantation or insertion into a vertebrate subject.

16. The medical device of claim 1, wherein said medical device is selected from a guide wire, a balloon, a vena cava filter, a catheter, a stent, a stent graft, a vascular graft, a cerebral aneurysm filler coil, a myocardial plug, a heart valve, a vascular valve, and a tissue engineering scaffold.

17. The medical device of claim 1, wherein the said particle-containing region is a conductive region.

18. The medical device of claim 17, wherein the said particle-containing region has a conductivity that ranges from $1\times10^4$ to $1\times10^6$ S/m.

19. The medical device of claim 17, further comprising, a second conductive region, and a therapeutic-agent-containing region comprising a charged therapeutic agent disposed between said second conductive region and said conductive particle containing region, wherein said device is configured to apply a voltage from said power source between said second conductive region and said conductive particle containing region.

20. The medical device of claim 19, wherein said second conductive region is a conductive substrate corresponding to a medical device or a portion thereof.

21. The medical device of claim 1 wherein the diamond-like coating has a hardness in the range of about 10 GPa to about 90 GPa.

22. The medical device of claim 1 wherein the diamond-like coating has a hardness of about 49 GPa or more.

23. The medical device of claim 1 wherein the particles in said layer have a maximum dimension of at least 100 nm.

24. The medical device of claim 1 wherein the particles in said layer have a minimum dimension of 10 micrometers or less.

25. The medical device of claim 1 wherein said medical device is an expandable medical device.

\* \* \* \* \*